(12) United States Patent
Polzius et al.

(10) Patent No.: US 11,751,805 B2
(45) Date of Patent: Sep. 12, 2023

(54) TRANSCUTANEOUS DETECTION SYSTEM

(71) Applicant: Dräger Safety AG & Co. KGaA, Lübeck (DE)

(72) Inventors: Rainer Polzius, Lübeck (DE); Michael Sick, Lübeck (DE); Jens Rekow, Lübeck (DE); Marie-Isabell Mattern-Frühwald, Lübeck (DE)

(73) Assignee: Dräger Safety AG & Co. KGaA, Lübeck (DE)

( * ) Notice: Subject to any disclaimer, the term of this patent is extended or adjusted under 35 U.S.C. 154(b) by 509 days.

(21) Appl. No.: 16/906,403

(22) Filed: Jun. 19, 2020

(65) Prior Publication Data

US 2020/0397368 A1   Dec. 24, 2020

(30) Foreign Application Priority Data

Jun. 21, 2019   (DE) .......................... 102019004331.6

(51) Int. Cl.
| | | |
|---|---|---|
| *A61B 5/145* | (2006.01) | |
| *A61B 5/00* | (2006.01) | |
| *A61B 5/1477* | (2006.01) | |
| *A61B 10/00* | (2006.01) | |
| *A61B 5/117* | (2016.01) | |
| *G01N 27/407* | (2006.01) | |
| *A61B 10/02* | (2006.01) | |

(52) U.S. Cl.
CPC ............ *A61B 5/4845* (2013.01); *A61B 5/117* (2013.01); *A61B 5/1477* (2013.01); *A61B 5/14521* (2013.01); *A61B 10/0064* (2013.01); *A61B 10/02* (2013.01); *G01N 27/407* (2013.01); *A61B 2560/0247* (2013.01); *A61B 2562/043* (2013.01)

(58) Field of Classification Search
CPC ... A61B 5/4845; A61B 10/0064; A61B 10/02; A61B 2560/0247; A61B 2562/043; A61B 5/117; A61B 5/14521; A61B 5/1477; G01N 27/407; G01N 33/4972
See application file for complete search history.

(56) References Cited

U.S. PATENT DOCUMENTS

| 5,944,661 | A | 8/1999 | Swette et al. | |
|---|---|---|---|---|
| 7,615,139 | B2 * | 11/2009 | Kiesele | G01N 27/404 204/411 |
| 2011/0154887 | A1 | 6/2011 | Cooper et al. | |
| 2011/0266160 | A1 * | 11/2011 | Campbell | G01N 33/49 205/785.5 |

(Continued)

FOREIGN PATENT DOCUMENTS

EP   1873528 A1   1/2008

*Primary Examiner* — Eric J Messersmith
(74) *Attorney, Agent, or Firm* — McGlew and Tuttle, P.C.

(57) ABSTRACT

A detection system (100) detects at least ethanol in human sweat. The detection system (100) includes at least one sensor (105) that is an electrochemical gas sensor. The at least one sensor (105) is configured at least for the detection of ethanol. The detection system (100) further includes a measuring chamber (107), in which substances excreted by the user via the user's skin can be fed via a waterproof, gas-permeable diffusion membrane to the at least one sensor (105). The detection system (100) further includes at least one seal (127), which is configured to be brought into direct contact with the skin of a user and to protect at least the measuring chamber (107) from environmental effects.

20 Claims, 3 Drawing Sheets

(56) References Cited

U.S. PATENT DOCUMENTS

| | | |
|---|---|---|
| 2013/0006066 A1 | 1/2013 | Melton |
| 2014/0128693 A1 | 5/2014 | Rompa, Jr. et al. |
| 2016/0000361 A1* | 1/2016 | Shnaper ............. A61B 5/14546 600/365 |
| 2016/0338627 A1* | 11/2016 | Lansdorp ................ A61B 5/681 |
| 2018/0008176 A1 | 1/2018 | Simpson et al. |
| 2019/0110721 A1* | 4/2019 | Nothacker ........... A61B 5/7275 |

* cited by examiner

TRANSCUTANEOUS DETECTION SYSTEM

CROSS REFERENCE TO RELATED APPLICATIONS

This application claims the benefit of priority under 35 U.S.C. § 119 of German Application 10 2019 004 331.6, filed Jun. 21, 2019, the entire contents of which are incorporated herein by reference.

TECHNICAL FIELD

The present invention pertains to a detection system for detecting at least ethanol in human sweat, to the use of the detection system for detecting at least ethanol in human sweat and to a detection process for detecting at least ethanol in human sweat.

TECHNICAL BACKGROUND

Detection systems for detecting a behavior of a user, for example, a prisoner, are used especially in law enforcement. For example, ankle shackles, which measure the excretion products excreted by a user, for example, sweat, by means of a sensor unit and transmit correspondingly collected measured data for analysis to an analysis unit, are known for this purpose.

Prior-art detection systems are arranged at a user, as a rule, in an air- and water-permeable manner, so that these are destroyed in a short time, for example, due to a leg equipped with a detection system being dipped into water.

Further, problems may arise during the use of prior-art detection systems due to environmental effects, for example, smoke or spilled alcohol, which may lead to a false positive report.

The document US 2014/0128693 A1 describes a system for receiving and analyzing transdermal secretions of a user, in which a baseline value is determined at first, as a function of which measured values detected later are interpreted.

The document US 2011/0154887 A1 describes a system for detecting signals of a user with a transdermal alcohol sensor.

The document U.S. Pat. No. 5,944,661 A describes a sensor for detecting transdermal alcohol.

SUMMARY

Based on the above-described state of the art, a basic object of the present invention is to provide a possibility for detecting an alcohol level of a user, which at least partially overcomes the above-described drawbacks. In particular, the basic object of the present invention is to provide a possibility for the reliable detection of an alcohol level of a particular user.

The above object is accomplished by a detection system and by a detection process according to the present invention and from the description and from the drawings. Features and details that are described in connection with the detection system also apply, of course, in connection with the detection process according to the present invention and vice versa, so that reference is and can mutually always be made to the individual aspects of the present invention concerning the disclosure.

In a first aspect, the invention being presented thus pertains to a detection system for detecting at least ethanol in human sweat. The detection system being presented comprises at least one first sensor, wherein the at least one first sensor is an electrochemical gas sensor, and wherein the at least one first sensor is configured at least for detecting ethanol. The detection system further comprises a measuring chamber, in which substances excreted by the user via his skin can be fed through a waterproof, gas-permeable diffusion membrane to the at least one first sensor. The detection system further comprises at least one seal, which is configured to be brought into direct contact with the skin of a user and to protect at least the measuring chamber from environmental effects.

Provisions are made, in particular, for the first sensor and/or for an optional second sensor to be configured as electrochemical sensors.

The detection system being presented is used especially to detect transdermal alcohol, which is excreted by a user. The detection system may be integrated to this end, for example, into an ankle shackle or a band. The detection system may, of course, also be configured for arrangement on any body part of a user, for example, an arm.

The detection of alcohol is defined in the context of the present invention as a procedure in which ethanol and/or decomposition products thereof are detected.

A measuring chamber, which is open in the direction of the user and is limited only by an apertured diaphragm, so that substances or secretions excreted by the user, especially sweat of the user, migrate into the measuring chamber and can be detected there by means of the first sensor provided there according to the present invention, is formed between the detection system according to the present invention and a user. Since the sweat of the user contains ethanol if the user consumed ethanol, the detection system can be used to infer a consumption behavior or an alcohol level of the user on the basis of ethanol detected in the sweat.

The detection system being presented comprises, in particular, only one measuring chamber.

The detection system being presented comprises at least one seal. The seal provided according to the present invention is arranged especially at the measuring chamber. This means that the seal surrounds the measuring chamber in at least some areas by the seal together with additional elements, for example, structural elements of the detection system, and, as a result, it forms the measuring chamber.

The measuring chamber is configured especially to guide sweat excreted by a user or corresponding secretions excreted by the user to the first sensor of the detection system being presented. This means that the detection system is configured to operate in the diffusion operation, so that no pumps are needed for taking up the sample. Gas, for example, sweat excreted by a user and having entered into a gaseous phase, can reach the first sensor at any time and be reacted and measured there directly in the diffusion operation of the detection system according to the present invention. The detection system correspondingly determines a value that is characteristic of ethanol as soon as ethanol molecules or decomposition products thereof in the sweat leave the skin of the user, so that a corresponding logging signal can be outputted in case a particular determined value is higher than a preset threshold value. Such a detection operation may last until ethanol ceases to diffuse through the skin of the user, so that, for example, the logging signal is outputted until ethanol ceases to diffuse through the skin of the user. This means that an exact time of sweating out ethanol can be detected on the basis of corresponding measured values or the logging signal. Furthermore, it is possible to determine the decomposition of ethanol based on the sweat of the user over time and accurately, for example, by a steady, i.e., continuous detection or by a consecutive detection at a high frequency of, e.g., one measurement per second.

Further, the filling up of components, for example, of a water reservoir, during the use time can be done away with with the use of the detection system being proposed, because the electrochemical sensor has a sufficient quantity of electrolyte. The detection system being presented can correspondingly be worn, for example, for 6 months or longer continuously and without maintenance.

The measuring chamber of the detection system being presented can be limited downwards by the skin of a user by the seal provided according to the present invention, so that the measuring chamber extends from the skin of the user, which makes possible an especially compact and small-volume configuration of the measuring system and correspondingly of the detection system being presented. The seal may be configured as a part of the measuring chamber.

The seal provided according to the present invention is configured especially to directly protect the measuring chamber from environmental effects.

Provisions are made for the first sensor provided according to the present invention to be shielded in a waterproof manner against a surrounding area via at least one diffusion membrane.

The diffusion membrane provided according to the present invention may be configured especially to seal the first sensor according to an IP66, IP67 or IP68 rating.

Provisions are made, in particular, for the first sensor provided according to the present invention to be selective for and sensitive to ethanol. The first sensor may be configured to this end, for example, as an amperometric sensor, which is more sensitive in a range of values characteristic of ethanol than in value ranges not characteristic of ethanol. Furthermore, the first sensor may be configured to output a logging signal when a measured value that is characteristic of ethanol is detected in order to log the detection of ethanol.

Provisions may be made for the at least one first sensor to comprise an electrode system, wherein the electrode system comprises a first working electrode for the selective detection of ethanol from among substances excreted by the user via his skin, a counterelectrode, a reference electrode for maintaining the potential at the working electrode, and a second working electrode. The second working electrode is configured to electrochemically process gases entering the measuring chamber from an area surrounding the detection system and, as a result of this, to protect the reference electrode from an effect of the gases.

The electrode system comprises a reference electrode for maintaining the potential at the working electrode and a second working electrode, which is configured to protect the reference electrode from the interfering entry of gases from the outside, for example, through a pressure equalization hole via a second diffusion membrane into the detection system and hence from behind to the first sensor. The second working electrode therefore acts as an intercepting electrode. The potential at the second electrode may be equal to or different from the potential of the first working electrode.

Provisions may be made for the detection system to comprise a second sensor, wherein the second sensor is arranged at the detection system such that it contacts an area surrounding the detection system in order to detect possibly occurring interfering gases from the area surrounding the detection system, and wherein the detection system comprises a control unit, which is configured to mathematically compare measured values of the interfering gases, which are detected by the second sensor, with measured values of the at least one first sensor and to take them into account.

A second electrochemical gas sensor may optionally be integrated in the detection system in order to prevent a distortion of measured values of a sweat sample excreted by a user, which occurs due to external effects, such as alcohol-containing liquids in an environment of the detection system being presented and are not excreted with the sweat, but are introduced into the first sensor via an outer side of the detection system. This second sensor may be placed on a side of the detection system facing away from the skin of the user and be used to measure external interfering effects. Interfering effects from the outside, e.g., spilled ethanol, can be eliminated from a measured value determined for sweat by the first sensor by a mathematical comparison of measured values of the second sensor with measured values of the first sensor, which may have a gas inlet in the direction of the measuring chamber. This makes it possible to avoid false positive and false negative results.

A contamination of a sweat sample that enters into the first sensor through the measuring chamber can be avoided by means of a seal completely enclosing an apertured diaphragm at the access to the measuring chamber. This seal may consist of a polymer nonwoven, a foam or another plastic. The seal ensures that the apertured diaphragm with the adjoining measuring chamber is adapted to the user in a form of a contact area and the detection system is connected by the seal to the user in a positive-locking manner and tightly and can be arranged at the user, as a result of which the wearing comfort is increased for the user and rapid entry of interfering substances into the measuring chamber is prevented.

The first sensor may be in contact with the measuring chamber through a diffusion membrane, which is tightly connected to the sensor. This diffusion membrane may consist, for example, of a hydrophobic, gas-permeable polymer, for example, polytetrafluoroethylene, which protects the sensor and hence the entire measuring unit from the entry of liquids. The first sensor and all components within the detection system, with the exception of the measuring chamber, are sealed, especially sealed in a waterproof manner, by this diffusion membrane or by a selectively permeable membrane.

The second sensor likewise comprises four electrodes and is in contact with an area surrounding the detection system being presented in order to detect an environmental effect or interfering gases, for example, smoke or carbon monoxide or alcohol (ethanol) splashed onto the system from the outside and optionally to correct measured values detected by the first sensor in the measuring chamber of the detection system. The first sensor and the second sensor may be connected to this end, for example, to a control unit or to a computer.

Furthermore, the detection system being presented may comprise a temperature and/or humidity sensor, which detects a temperature and/or humidity present in the measuring chamber. Additional measured values, for example, measured values determined by means of the first sensor in the measuring chamber, can be validated and optionally corrected by means of correspondingly detected values of the temperature and/or humidity in the measuring chamber.

Furthermore, provisions may be made for the detection system to comprise a control unit, which is configured to activate the second sensor only if the first sensor is currently detecting ethanol. The control unit may comprise one or more processors and memory.

In order to optimize, for example, the energy consumption of the detection system being presented, provisions may be made for a respective second sensor of the detection system being activated or being able to be activated only when this second sensor is also actually needed. An activation of the second sensor may be carried out to this end, for example, when a measured value currently being detected by the first sensor is higher than a predefined threshold value.

Provisions may, furthermore, be made for the detection system to comprise a heating element, which is configured to heat the measuring chamber in at least some areas.

Condensation can be prevented in the detection system being presented in at least some areas by means of a heating element, which may be configured, for example, as an electrical resistor, for example, as a wire coil, as a lighting element or as a carbon heater. Since condensates, for example, sweat, occur especially in the area of the measuring chamber of the detection system, the heating element is arranged in the area of the measuring chamber. This means that the measuring chamber and the diffusion membrane leading to the first sensor can be kept permeable to gases, especially to air and alcohol molecules in the sweat, by means of a heating element.

Furthermore, provisions may be made for at least one collection matrix to be replaceably arranged in the measuring chamber for receiving excretion products of the user. The detection system may comprise in this case a mechanism for removing the collection matrix from the measuring chamber and/or for inserting a collection matrix into the measuring chamber.

Substances from the sweat of a user as well as skin cells of the user can be collected and stored by means of the collection matrix, which may consist, for example, of cellulose, cotton or a polymer, for example, a polyolefin or a polyester. The collection matrix may be arranged in the measuring chamber to this end, for example, such that it is not directly in contact with the skin of the user but is shielded by the measuring chamber, especially by the apertured diaphragm of the detection system, from a surrounding area and is correspondingly protected from contamination by a surrounding area.

The detection system may comprise a mechanism, for example, a closable opening or a plug-in unit, for replacing the collection matrix.

In case of, for example, a service interval of the detection system being presented, the collection matrix can be removed and replaced with a fresh collection matrix and tested in an outside testing laboratory, for example, for illicit narcotic substances and decomposition products thereof, for example, *cannabis*, opiates, cocaine, amphetamines, benzodiazepines, tricyclic antidepressants and ethyl glucocuronide as long-term markers of alcohol or other substances. Furthermore, the identity of the user can be inferred from a DNA contained in the skin cells being stored in the collection matrix.

Provisions may be made for the at least one collection matrix to be configured as a hydrophilic and/or capillary active storage element for collecting sweat and/or skin cells of the user. The collection matrix may be arranged to this end in the detection system such that the at least one collection matrix is in direct contact with the skin of the user.

Due to a capillary active collection matrix, skin cells can at least be held by means of the capillary force and possibly separated from a user, so that the skin cells are stored in the collection matrix. The collection matrix may have, for example, a porous configuration to this end. An especially rapid and selective transfer of hydrophilic substances from the sweat of the user into the collection matrix can be achieved by a hydrophilic collection matrix, i.e., a collection matrix that consists of a hydrophilic substance.

Provisions may, furthermore, be made for the at least one collection matrix to be arranged at the apertured diaphragm.

An especially strong contact can be achieved between the collection matrix and the skin of a user due to the collection matrix being arranged at the measuring chamber provided according to the present invention, in which the collection matrix is in direct contact with the apertured diaphragm due to a force of pressure, by which the collection matrix is pressed onto the skin of the user, being transmitted to the collection matrix by the apertured diaphragm.

Provisions may, furthermore, be made for the first sensor to comprise a stacked array of electrodes and nonwoven layers arranged in parallel, wherein a porous membrane, which is permeable to air, is in contact with the stacked array of electrodes and nonwoven layers arranged in parallel on at least one side, at least one layer of a hydrophilic nonwoven is arranged between respective electrodes of the first sensor, and the electrodes, the hydrophilic nonwoven and the porous, air-permeable membrane have essentially each a circular area, wherein the porous, air-permeable membrane and the hydrophilic nonwoven additionally have strips arranged in a star-shaped pattern from the edge of each circular area, so that the porous, air-permeable membrane and the hydrophilic nonwoven extend into a separate, at least partially electrolyte-filled compensating volume, which is located at least partially in one plane with the electrodes, encloses in this plane the electrode array at least partially in the circumferential direction, and the porous, air-permeable membrane is exposed to ambient pressure in at least some areas.

Escape of electrolyte being stored in the detection system, for example, in the direction of the skin of a user, as well as the entry of water into the sensor can be prevented by means of a porous, air-permeable, hydrophobic diffusion membrane.

In a second aspect, the invention being presented pertains to the use of the detection system being presented for detecting ethanol in the sweat of a user of the detection system. The detection system may be configured to this end, for example, for detecting ethanol molecules and/or decomposition products thereof.

The present invention pertains therefore to the use of the detection system being presented for detecting ethanol in the sweat of a user of the detection system, wherein the detection system comprises at least one first sensor, wherein the at least one first sensor is an electrochemical gas sensor, wherein the at least one first sensor is configured at least for detecting ethanol, wherein the detection system comprises a measuring chamber, in which substances excreted by the user via his skin can be fed through a waterproof, gas-permeable diffusion membrane to the at least one first sensor, wherein the detection system further comprises at least one seal, which is configured to be brought into direct contact with the skin of a user and to protect at least the measuring chamber from environmental effects.

In a third aspect, the invention being presented pertains to the use of the detection system being presented for detecting ethanol and at least one other substance. The additional substance may be selected here from a predefined list of substances, for example, *cannabis*, cocaine, amphetamines or decomposition products thereof.

In a fourth aspect, the invention being presented pertains to a detection process for detecting at least ethanol in the sweat of a user by means of the detection system being presented, wherein the detection process comprises the application of the detection system to the user and the detection of at least ethanol by means of a sensor of the detection system.

Provisions may, furthermore, be made for the detection process to comprise, further, the collection of excretion products of the user by means of a collection matrix of the detection system, removal of the collection matrix from the detection system and the outside analysis of the excretion products collected in the collection matrix for at least one substance.

The substance may be selected from a predefined list of substances, for example, *cannabis*, cocaine, amphetamines or decomposition products thereof.

Furthermore, provisions may be made for the detection process to comprise and further make possible the checking of the identity of the user on the basis of the excretion products collected in the collection matrix.

Further steps improving the present invention arise from the following description of some exemplary embodiments of the present invention, which are shown in the figures. All the features and/or advantages appearing from the claims, from the description or from the drawings, including design details and arrangements in space, may be essential for the present invention both in themselves and in the different combinations. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF PREFERRED EMBODIMENTS

Figure 1:
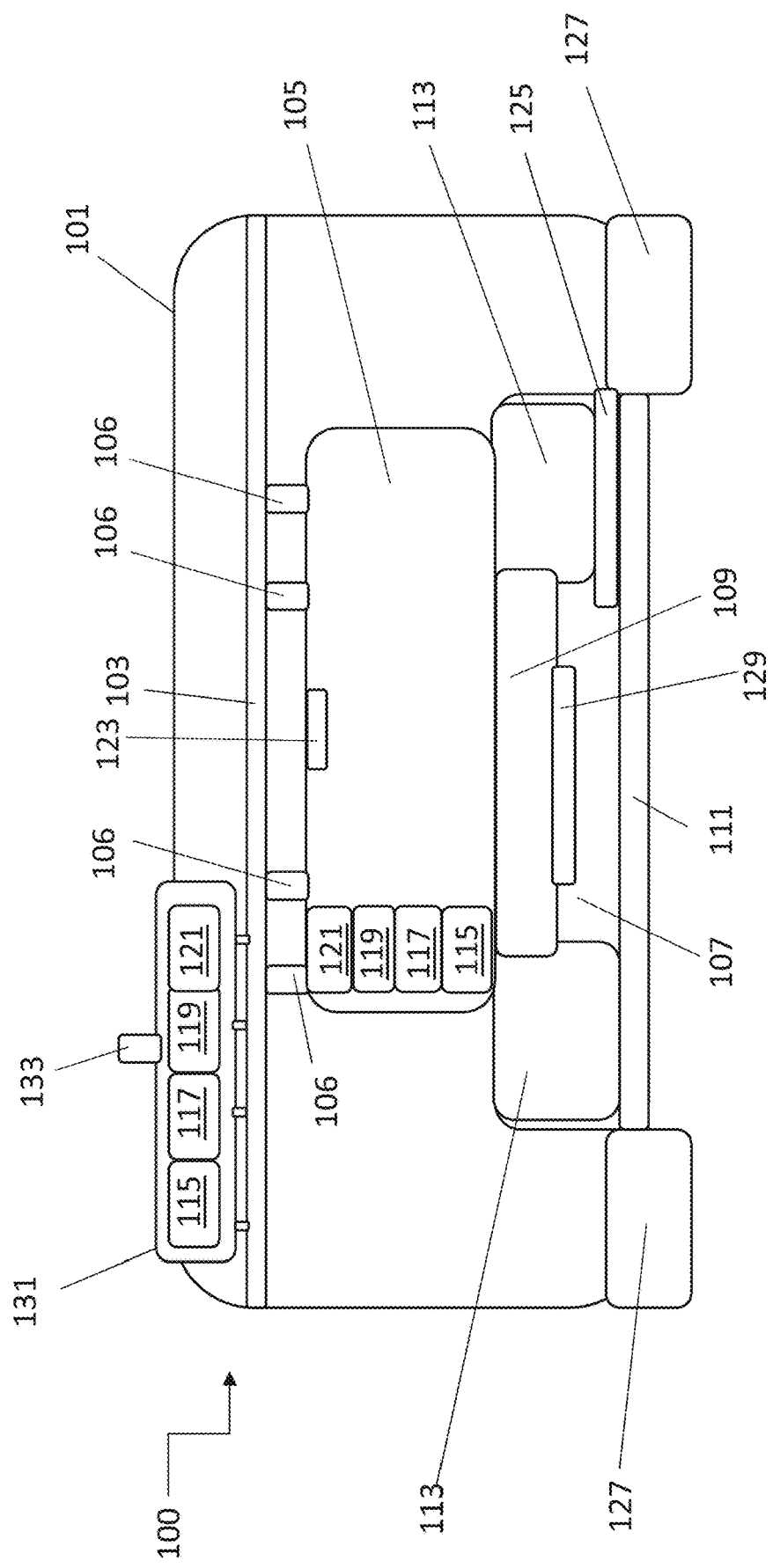
FIG. 1 is a schematic view of a possible embodiment of the detection system according to the present invention.

Referring to the drawings, FIG. 1 shows a detection system 100. The detection system 100 comprises a housing 101, at which a printed circuit board 103, which is connected to a first sensor 105, is arranged.

The first sensor 105 can be supplied with electric current or electrical energy and/or controlled, i.e., regulated or controlled, through the printed circuit board 103 by means of electrical contacts 106. The printed circuit may comprise a control unit with one or more processors and memory.

Further, the detection system 100 comprises a measuring chamber 107, which may have a diffusion membrane 109, which acts as a gas inlet to the first sensor 105 and is permanently connected to this, in the direction of the sensor 105 and may have an apertured diaphragm 111 in the direction of the skin of a user.

The measuring chamber 107 is limited, in particular, by the apertured diaphragm 111 and during use by the skin of the user as the lower boundary layer and by the diffusion membrane 109 at the first sensor 105 as the upper boundary layer. Further, the measuring chamber 107 may be defined by structural elements.

The diffusion membrane 109 may be configured such that the diffusion membrane 109 prevents the passage of liquids, for example, an electrolyte contained in the detection system 100, to the skin of the user and prevents entry of water into the first sensor 105.

The diffusion membrane 109 may consist of hydrophobic, gas-permeable polymers, for example, polytetrafluoroethylene, polypropylene or polyethylene.

The apertured diaphragm 111 may be shaped, for example, corresponding to the body shape of the user, so that the detection system 100 is in a positive-locking or close contact with the user.

When the detection system 100 is being worn while the user consumes alcohol, ethanol molecules and/or decomposition products thereof are excreted with the sweat of the user through the skin of the user. Gaseous sweat and ethanol molecules as well as decomposition products of ethanol molecules contained in the sweat diffuse from the skin through the apertured diaphragm 111 into the measuring chamber 107 and farther from there through the diffusion membrane 109 into the first sensor 105. The first sensor 105 is especially sensitive to and selective for ethanol molecules and/or decomposition products thereof, so that the first sensor 105 yields a measured value or has a deflection and outputs, for example, a logging signal, which leads to the storage of measured values determined by the first sensor 105.

Furthermore, a collection matrix 113, by which the substances excreted by a user, for example, sweat and skin cells, can be collected and stored, may be provided in the measuring chamber 107. The identity of a user can be determined without any doubt on the basis of skin cells being stored in the collection matrix 113, for example, by means of an outside DNA analysis, so that measured data determined by the detection system 100 can be assigned to a particular user without any doubt.

Further, a consumption behavior of a user, especially in respect to illicit and/or narcotic substances, can be analyzed on the basis of substances being stored in the collection matrix 113. The collection matrix may be used to this end, for example, for carrying out a drug screening.

The first sensor 105 is configured as an electrochemical four-electrode sensor and comprises a first working electrode 115, which is configured for the selective detection of ethanol, i.e., ethanol molecules and/or decomposition products thereof. Furthermore, the first sensor 105 comprises a counterelectrode 117, a reference electrode 119 for maintaining a potential at the working electrode and at a second working electrode 121, which acts as an intercepting electrode and protects the reference electrode 119 from effects of gases from the environment.

The first sensor 105 may be filled with a liquid electrolyte.

A second sensor 131, which is schematically shown in FIG. 1, is likewise an electrochemical sensor, which comprises at least three electrodes or more, in the case being shown here four electrodes. The arrangement of the electrodes corresponds to the configuration of the first sensor 105.

The second sensor 131 is adapted with contact points at the printed circuit board and the mode of operation is the same as or similar to that of the first sensor 105. The second sensor 131 differs from the first sensor 105 especially by the second sensor position in the detection system 100. The second sensor 131 is arranged especially on an environmental side, for example, on a side located opposite the skin of the user, and is arranged at a correspondingly spaced location from the first sensor 105.

A gas inlet 133 of the second sensor 131 is not in the direction of the skin, in particular, the direction of the gas inlet 133 is not in the direction of the first sensor gas inlet provided in the first sensor 105, but is instead directed in the opposite direction, in the direction of the outer side of the detection system 100.

External gases, which may possibly influence a measurement at the skin by the first sensor 105, are discharged via another diffusion membrane, which consists of a hydrophobic and gas-permeable plastic. This additional diffusion membrane also protects the outer side of the detection system from the entry of water.

Measured values determined by the first sensor 105 can be validated or corrected on the basis of measured values determined by the second sensor 131. For example, measured values determined by the second sensor 131 can be deducted for this from respective measured values determined by the first sensor 105.

Further, the first sensor 105 comprises a pressure equalization hole 123, through which gases formed in the first sensor 105 can escape into a surrounding area.

Further, a temperature and humidity sensor 125, by means of which current measurement conditions within the measuring chamber 107 can be detected and logged, is arranged in the measuring chamber 107.

The detection system 100 is shielded in the direction of the skin of the user, i.e., on the side of the skin, by a seal in the form of a sealing matrix 127. The sealing matrix 127 may consist of a flexible material, for example, polymer nonwoven or rubber, and is used to extensively shield the detection system 100 and especially the measuring chamber 107 from environmental effects, for example, smoke or liquids.

A heating element 129, which can possibly cause the sweat condensate collected in the measuring chamber 107 to evaporate, as a result of which gaseous sweat can diffuse through the diffusion membrane 109 into the first sensor 105, may be arranged at the diffusion membrane 109 of the first sensor 105.

The detection system 100 may be arranged, for example, on a band and worn by a user on the leg or on the arm.

Figure 2:
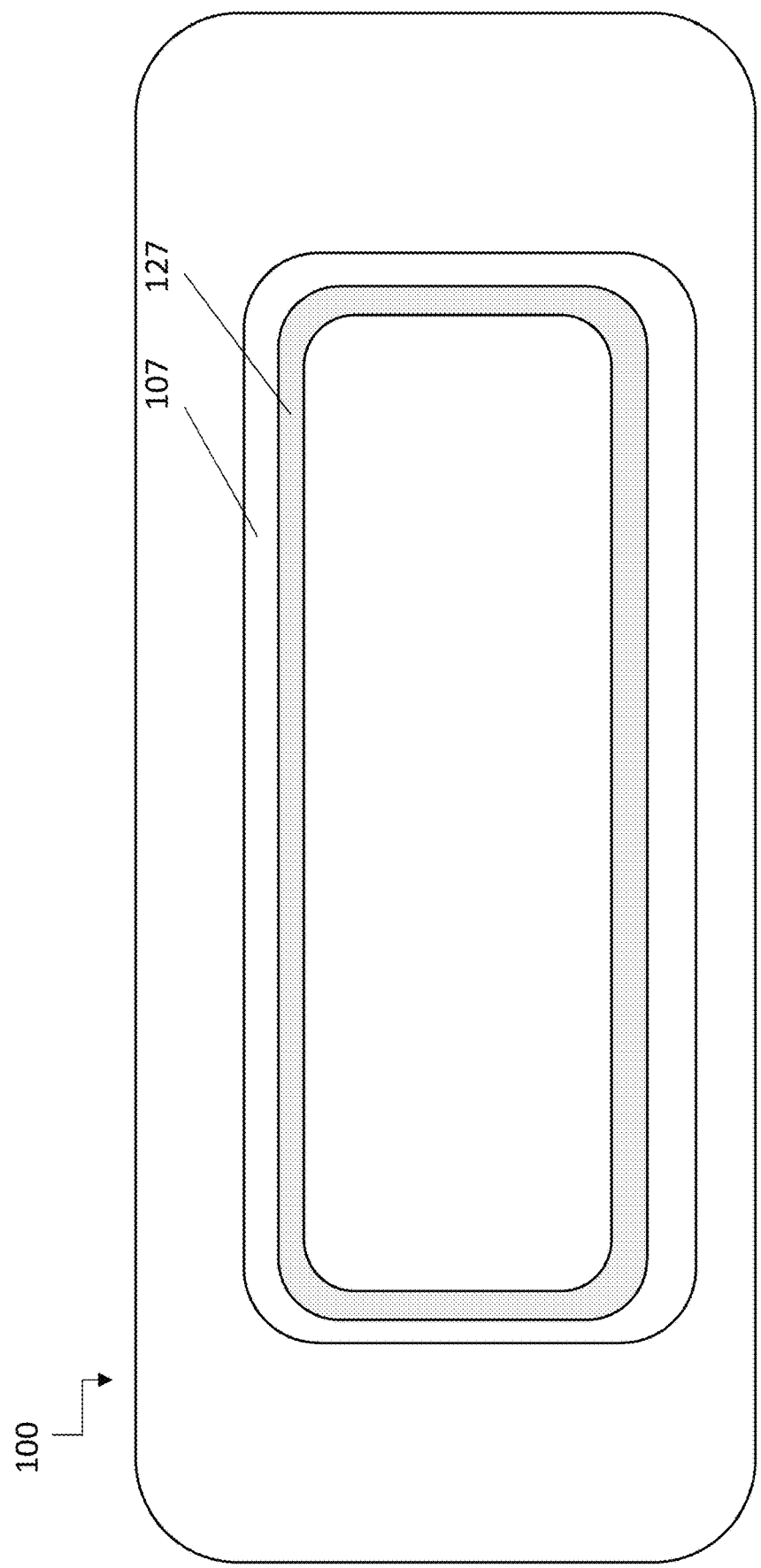
FIG. 2 is a schematic top view of the detection system according to FIG. 1.

The detection system 100 is shown in a top view in FIG. 2. It can be seen here that the collection matrix 113 completely encloses one of the measuring chambers 107, so that the collection matrix 113 also shields an inner area of the measuring chamber 107 against a surrounding area.

Figure 3:
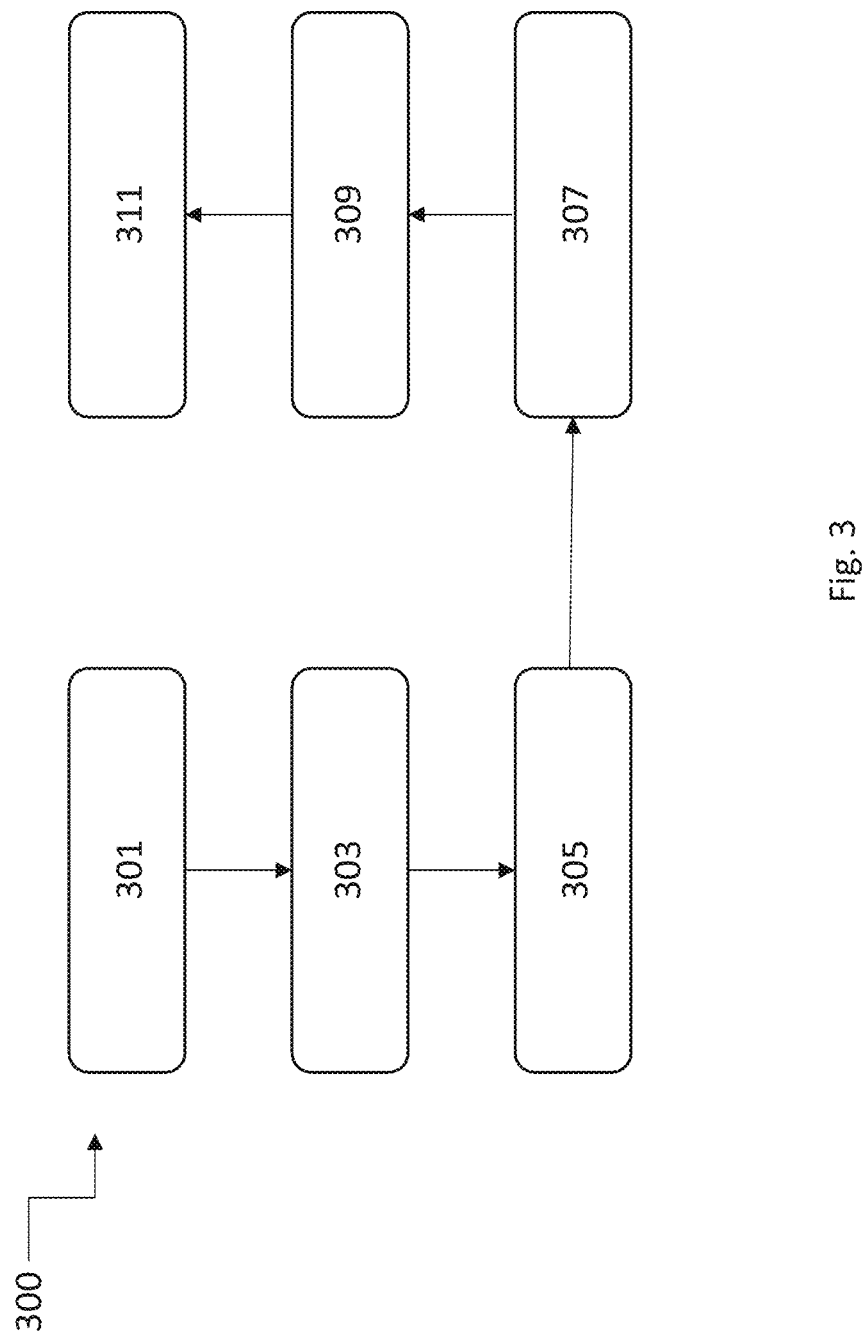
FIG. 3 is a flow diagram showing a possible embodiment of the detection process according to the present invention.

FIG. 3 shows a schematic procedure of the detection process 300 being presented.

The detection system 100, as is shown in FIG. 1, is placed on a user. The detection system 100 may be arranged to this end on a leg of the user, for example, by means of a band or an ankle shackle.

Detection of at least ethanol is carried out by means of the first sensor 105 of the detection system 100 in a detection step 303. A consumption behavior of the user with respect to ethanol can be analyzed on the basis of the measured values detected in step 303 immediately or at a later time.

Excretion products of a user are collected by means of the collection matrix 113 of the detection system 100 in an optional collection step 305.

The collection matrix 113 is removed from the detection system 100 via a reclosable access of the detection system 100 in an optional removal step 307.

Excretion products collected in the collection matrix 113 are tested for at least one substance in an optional analysis step 309.

The substance may be selected here from a predefined list of substances, for example, *cannabis*, cocaine, amphetamines or decomposition products thereof.

The identity of the user is determined in an optional identification step 311 on the basis of skin cells collected in the collection matrix 113 and of DNA contained in the skin cells.

While specific embodiments of the invention have been shown and described in detail to illustrate the application of the principles of the invention, it will be understood that the invention may be embodied otherwise without departing from such principles.

LIST OF REFERENCE NUMBERS

| | |
|---|---|
| 100 | Detection system |
| 101 | Housing |
| 103 | Printed circuit board |
| 105 | First sensor |
| 106 | Electrical contact |
| 107 | Measuring chamber |
| 109 | Diffusion membrane |
| 111 | Apertured diaphragm |
| 113 | Collection matrix |
| 115 | First working electrode |
| 117 | Counterelectrode |
| 119 | Reference electrode |
| 121 | Second working electrode |
| 123 | Pressure equalization hole |
| 125 | Humidity sensor |
| 127 | Sealing matrix |
| 129 | Heating element |
| 131 | Second sensor |
| 133 | Gas inlet |
| 300 | Detection process |
| 301 | Placement step |
| 303 | Detection step |
| 305 | Collection step |
| 307 | Removal step |
| 309 | Analysis step |
| 311 | Identification step |

What is claimed is:

1. A detection system for detecting at least ethanol in human sweat, the detection system comprising:
    at least one sensor comprising an electrochemical gas sensor, wherein the at least one sensor is configured for detecting ethanol;
    a measuring chamber with a waterproof, gas-permeable diffusion membrane, wherein the measuring chamber and the waterproof, gas-permeable diffusion membrane are configured such that substances excreted by the user via the user's skin are fed through the waterproof, gas-permeable diffusion membrane to the at least one sensor, at least a portion of the waterproof, gas-permeable diffusion membrane being located directly adjacent to the at least one sensor;
    a diaphragm located at a spaced location from the waterproof, gas-permeable diffusion member, the waterproof, gas-permeable diffusion membrane and the diaphragm defining at least a portion of the measuring chamber; and
    at least one seal configured to be brought into direct contact with the skin of a user and to protect at least the measuring chamber from environmental effects.

2. A detection system in accordance with claim 1, wherein the at least one sensor comprises an electrode system comprising:
- a first working electrode for the selective detection of ethanol from the user from substances excreted by the user via his skin;
- a counterelectrode;
- a reference electrode for maintaining a potential at the working electrode;
- a second working electrode, which is configured to electrochemically process gases entering the measuring chamber from an area surrounding the detection system so as to protect the reference electrode from an effect of the gases.

3. A detection system in accordance with claim 1, further comprising:
- a second sensor arranged to contact an area surrounding the detection system in order to detect possibly occurring interfering gases from the area surrounding the detection system; and
- a control unit to mathematically compare measured values of the interfering gases, which measured values are detected by the second sensor, with measured values of the at least one sensor.

4. A detection system in accordance with claim 3, wherein the control unit is configured to activate the second sensor only when the at least one sensor detects ethanol.

5. A detection system in accordance with claim 3, wherein the at least one sensor and the second sensor are configured as amperometric multielectrode sensors.

6. A detection system in accordance with claim 1, further comprising at least one heating element configured to heat the measuring chamber in at least some areas.

7. A detection system in accordance with claim 1, further comprising:
- at least one collection matrix arranged replaceably in the measuring chamber for receiving excretion products of the user;
- a mechanism for removing the collection matrix from the measuring chamber and/or for inserting a collection matrix into the measuring chamber.

8. A detection system in accordance with claim 7, wherein the at least one collection matrix is configured as a hydrophilic and/or capillary active storage element for collecting sweat and skin cells of the user and is arranged such that the at least one collection matrix contacts the skin of the user directly.

9. A detection system in accordance with claim 8, wherein the at least one collection matrix is arranged at the at least one diffusion membrane.

10. A detection system in accordance with claim 1, wherein:
- the at least one sensor comprises a stacked array of electrodes and nonwoven layers arranged in parallel;
- a porous, air-permeable membrane is in contact on at least one side with the stacked array of electrodes and nonwoven layers arranged in parallel, at least one layer of a hydrophilic nonwoven is arranged between respective electrodes of the sensor, and the electrodes, the hydrophilic nonwoven and the porous, air-permeable membrane each have essentially a circular area;
- the porous, air-permeable membrane and the hydrophilic nonwoven have strips arranged in a star-shaped pattern from the edge of each circular area, so that the porous, air-permeable membrane and the hydrophilic nonwoven extend into a separate, at least partially electrolyte-filled compensating volume, which is located at least partially in one plane with the electrodes, surrounds the electrode array in this plane at least partially in the circumferential direction, and the porous, air-permeable membrane is exposed to ambient pressure in at least some areas.

11. A detection system in accordance with claim 1, wherein the detection system detects ethanol in the sweat of a user of the detection system.

12. A detection system in accordance with claim 7, wherein the detection system detects ethanol in the sweat of a user of the detection system and another property.

13. A detection system in accordance with claim 1, further comprising:
- at least one collection matrix arranged replaceably in the measuring chamber for receiving excretion products of the user.

14. A detection process for detecting at least ethanol in the sweat of a user, the detection process comprises the steps of:
- providing a detection system comprising: at least one first sensor comprising an electrochemical gas sensor, wherein the at least one sensor is configured for detecting ethanol; a measuring chamber with a waterproof, gas-permeable diffusion membrane, wherein the measuring chamber and the waterproof, gas-permeable diffusion membrane are configured such that substances excreted by the user via the user's skin are fed through the waterproof, gas-permeable diffusion membrane to the at least one sensor, at least a portion of the waterproof, gas-permeable diffusion membrane being located adjacent to the at least one sensor; a diaphragm located a spaced location from the waterproof, gas-permeable diffusion membrane, the waterproof, gas-permeable diffusion membrane and the diaphragm defining at least a portion of the measuring chamber; and at least one seal configured to be brought into direct contact with the skin of a user and to protect at least the measuring chamber from environmental effects;
- placing the detection system on the user; and
- detecting at least ethanol by means of the sensor of the detection system.

15. A detection process in accordance with claim 14, wherein the detection system, further comprises: at least one collection matrix arranged replaceably in the measuring chamber for receiving excretion products of the user; and a mechanism for removing the collection matrix from the measuring chamber and/or for inserting a collection matrix into the measuring chamber and the detection process further comprises:
- collecting excretion products of the user by means of the collection matrix of the detection system;
- removing the collection matrix from the detection system; and
- analyzing the excretion products collected in the collection matrix for at least one substance.

16. A detection process in accordance with claim 15, further comprising checking an identity of the user on the basis of the excretion products collected in the collection matrix.

17. A detection process in accordance with claim 14, wherein the detection system further comprises at least one collection matrix arranged replaceably in the measuring chamber for receiving excretion products of the user.

18. A detection process in accordance with claim 14, wherein the diaphragm is in contact with the at least one seal.

19. A detection system for detecting at least ethanol in human sweat, the detection system comprising:

at least one sensor comprising an electrochemical gas sensor, wherein the at least one sensor is configured for detecting ethanol;

a measuring chamber with a waterproof, gas-permeable diffusion membrane, wherein the measuring chamber and the waterproof, gas-permeable diffusion membrane are configured such that substances excreted by the user via the user's skin are fed through the waterproof, gas-permeable diffusion membrane to the at least one sensor;

at least one seal configured to be brought into direct contact with the skin of a user and to protect at least the measuring chamber from environmental effects; and at least one collection matrix arranged replaceably in the measuring chamber for receiving excretion products of the user.

20. A detection system in accordance with claim 19, further comprising:

a mechanism for removing the collection matrix from the measuring chamber and/or for inserting a collection matrix into the measuring chamber.

* * * * *